United States Patent
Toreki et al.

(10) Patent No.: US 9,873,751 B2
(45) Date of Patent: Jan. 23, 2018

(54) SUPERABSORBENT MATERIALS COMPRISING PEROXIDE

(71) Applicant: Quick-Med Technologies, Inc., Gainesville, FL (US)

(72) Inventors: William Toreki, Gainesville, FL (US); Susan Leander, Gainesville, FL (US); Gerald M. Olderman, Bedford, MA (US)

(73) Assignee: Quick-Med Technologies, Inc., Gainesville, FL (US)

( * ) Notice: Subject to any disclaimer, the term of this patent is extended or adjusted under 35 U.S.C. 154(b) by 0 days.

(21) Appl. No.: 14/541,764

(22) Filed: Nov. 14, 2014

(65) Prior Publication Data

US 2015/0071870 A1    Mar. 12, 2015

Related U.S. Application Data

(60) Division of application No. 12/796,708, filed on Jun. 9, 2010, which is a continuation-in-part of application No. PCT/US2010/024635, filed on Feb. 18, 2010.

(60) Provisional application No. 61/153,464, filed on Feb. 18, 2009.

(51) Int. Cl.
| | |
|---|---|
| *A61K 9/00* | (2006.01) |
| *C08F 8/00* | (2006.01) |
| *A61L 15/60* | (2006.01) |
| *A61L 15/46* | (2006.01) |
| *A01N 37/02* | (2006.01) |
| *A01N 59/00* | (2006.01) |
| *A61K 33/40* | (2006.01) |
| *A61K 47/48* | (2006.01) |
| *A61L 15/24* | (2006.01) |
| *A61L 15/44* | (2006.01) |
| *C08L 33/08* | (2006.01) |
| *C08L 33/10* | (2006.01) |

(52) U.S. Cl.
CPC ............ *C08F 8/00* (2013.01); *A01N 37/02* (2013.01); *A01N 59/00* (2013.01); *A61K 33/40* (2013.01); *A61K 47/48176* (2013.01); *A61L 15/24* (2013.01); *A61L 15/44* (2013.01); *A61L 15/46* (2013.01); *A61L 15/60* (2013.01); *A61K 2800/56* (2013.01); *A61L 2300/11* (2013.01); *A61L 2300/404* (2013.01); *A61L 2300/802* (2013.01); *C08L 33/08* (2013.01); *C08L 33/10* (2013.01); *Y10T 428/1324* (2015.01)

(58) Field of Classification Search
None
See application file for complete search history.

(56) References Cited

U.S. PATENT DOCUMENTS

| | | |
|---|---|---|
| 2,976,576 A | 3/1961 | Wichterle et al. |
| 2,988,539 A | 6/1961 | Cohen et al. |
| 3,220,960 A | 11/1965 | Wichterle et al. |
| 3,393,168 A | 7/1968 | Johnson |
| 3,514,419 A | 5/1970 | Darlow et al. |
| 3,557,067 A | 1/1971 | Burns |
| 3,783,872 A | 1/1974 | King |
| 3,900,378 A | 8/1975 | Yen et al. |
| 3,966,679 A | 6/1976 | Gross |
| 3,993,616 A | 11/1976 | Gross |
| 4,069,177 A | 1/1978 | Smith |
| 4,076,663 A | 2/1978 | Masuda et al. |
| 4,115,332 A | 9/1978 | Young et al. |
| 4,117,222 A | 9/1978 | Holst et al. |
| 4,154,898 A | 5/1979 | Burkholder, Jr. |
| 4,167,464 A | 9/1979 | George |
| 4,172,841 A | 10/1979 | Danna et al. |
| 4,174,418 A | 11/1979 | Welch et al. |
| 4,192,727 A | 3/1980 | Ward |
| 4,192,827 A | 3/1980 | Mueller et al. |
| 4,199,322 A | 4/1980 | Danna et al. |
| 4,235,237 A | 11/1980 | Mesek et al. |
| 4,401,793 A | 8/1983 | Chiao et al. |
| 4,449,977 A | 5/1984 | Korpman |
| 4,529,739 A | 7/1985 | Scott et al. |
| 4,654,039 A | 3/1987 | Brandt et al. |

(Continued)

FOREIGN PATENT DOCUMENTS

| | | |
|---|---|---|
| CN | 1157575 A | 8/1997 |
| CN | 1791708 A | 6/2006 |
| CN | 1906243 A | 1/2007 |
| CN | 1921895 A | 2/2007 |
| EP | 0739635 A1 | 10/1996 |
| JP | H06-505765 | 6/1994 |
| JP | H10-509915 | 9/1998 |
| JP | 2001505606 | 4/2001 |
| WO | 98/20915 | 5/1998 |
| WO | 199908726 | 2/1999 |
| WO | 2003053481 A1 | 7/2003 |

(Continued)

OTHER PUBLICATIONS

Mustafa Arifoglu et al., "Reaction of Thiourea with Hydrogen Peroxide: 13C NMR Studies of an Oxidative/Reductive Bleaching Process" Textile Res. J. 62(2), 94-100 (1992).

(Continued)

*Primary Examiner* — James W Rogers
(74) *Attorney, Agent, or Firm* — Gerry J. Elman; M. P. Moon; Elman Technology Law, P.C.

(57) ABSTRACT

This invention pertains to a polymeric composition and an antimicrobial composition, each comprising a superabsorbent polymer (SAP), such as used in diapers and sanitary napkins, and peroxide. The superabsorbent material can be made by the process of treating a preformed SAP, such as a crosslinked polyacrylate salt, with a treatment solution comprising hydrogen peroxide dissolved in water, followed by drying. The resulting superabsorbent material has strong antimicrobial activity. Optionally, the treatment solution may also contain a metal salt, including those of zinc, zirconium, and magnesium.

4 Claims, 1 Drawing Sheet

(56) References Cited

U.S. PATENT DOCUMENTS

| | | | |
|---|---|---|---|
| 4,842,593 | A | 6/1989 | Jodan et al. |
| 4,981,485 | A | 1/1991 | Motono |
| 4,985,023 | A | 1/1991 | Blank et al. |
| 4,990,338 | A | 2/1991 | Blank et al. |
| 5,035,892 | A | 7/1991 | Blank et al. |
| 5,045,322 | A | 9/1991 | Blank et al. |
| 5,061,487 | A | 10/1991 | Blank et al. |
| 5,079,004 | A | 1/1992 | Blank et al. |
| 5,152,996 | A | 10/1992 | Corey et al. |
| 5,293,885 | A | 3/1994 | Darkwa et al. |
| 5,373,066 | A | 12/1994 | Rebre et al. |
| 5,442,014 | A | 8/1995 | Rebre et al. |
| 5,599,335 | A | 2/1997 | Goldman et al. |
| 5,656,037 | A | 8/1997 | Vigo et al. |
| 5,669,894 | A | 9/1997 | Goldman et al. |
| 6,043,209 | A | 3/2000 | Micciche et al. |
| 6,350,794 | B1 | 2/2002 | Borja |
| 6,399,092 | B1 | 6/2002 | Hobson et al. |
| 7,429,632 | B2 | 9/2008 | Mitchell |
| 7,799,095 | B2 | 9/2010 | Mario et al. |
| 2003/0135172 | A1 | 7/2003 | Whitmore et al. |
| 2004/0185735 | A1 | 9/2004 | Nakashima et al. |
| 2005/0090586 | A1* | 4/2005 | Kang ...................... A61L 15/60 524/27 |
| 2005/0113277 | A1 | 5/2005 | Sherry et al. |
| 2005/0124724 | A1 | 6/2005 | Burton et al. |
| 2005/0214382 | A1 | 9/2005 | Xia et al. |
| 2006/0089611 | A1 | 4/2006 | Herfert et al. |
| 2007/0020452 | A1 | 1/2007 | Hamed et al. |
| 2007/0077428 | A1 | 4/2007 | Hamed et al. |
| 2007/0110779 | A1 | 5/2007 | Bobbert |
| 2007/0128515 | A1 | 6/2007 | Lang et al. |
| 2008/0081848 | A1 | 4/2008 | Shih et al. |

FOREIGN PATENT DOCUMENTS

| | | | |
|---|---|---|---|
| WO | 20041064882 A1 | 8/2004 | |
| WO | WO 2007024972 A2 * | 3/2007 | ............. A61L 15/44 |
| WO | 2008058565 A1 | 5/2008 | |

OTHER PUBLICATIONS

Kunio Nakagawa and Kyaji Minami, "Reduction of Organic Compounds with Thiourea Dioxide. I. Reduction of Ketones to Secondary Alcohols" Tetrahedron Letters No. 5, 343-346 (1972).

* cited by examiner

SUPERABSORBENT MATERIALS COMPRISING PEROXIDE

CROSS-REFERENCE TO RELATED APPLICATIONS

This application is a Divisional of our co-pending U.S. application Ser. No. 12/796,708 filed Jun. 9, 2010, which is a Continuation-in-Part of International Patent Application, Serial Number PCT/US2010/024635, filed Feb. 18, 2010, which is a non-provisional application of U.S. Provisional Patent Application 61/153,464 filed Feb. 18, 2009. This application claims benefit of priority to each of the prior applications. The entire disclosures of each of the aforementioned applications are incorporated herein by reference.

TECHNICAL FIELD

This invention pertains to antimicrobial superabsorbent materials.

BACKGROUND ART

Water-absorbing resins are widely used in sanitary goods, diapers, hygienic goods, wiping cloths, packaging materials, water-retaining agents, dehydrating agents, sludge coagulants, disposable towels and bath mats, disposable door mats, thickening agents, disposable litter mats for pets, condensation-preventing agents, and release control agents for various chemicals. Water-absorbing resins are available in a variety of chemical forms, including substituted and unsubstituted natural and synthetic polymers, such as hydrolysis products of starch acrylonitrile graft polymers, carboxymethylcellulose, crosslinked polyacrylates, sulfonated polystyrenes, hydrolyzed polyacrylamides, polyvinyl alcohols, polyethylene oxides, polyvinylpyrrolidones, and polyacrylonitriles.

Such water-absorbing resins are termed "superabsorbent polymers," or SAPs, and typically are lightly crosslinked hydrophilic polymers. SAPs are materials that imbibe or absorb at least 10 times their own weight in aqueous fluid and that retain the imbibed or absorbed aqueous fluid under moderate pressure. The imbibed or absorbed aqueous fluid is taken into the molecular structure of the SAP rather than being contained in pores from which the fluid could be eliminated by squeezing. Some SAPs can absorb up to 1,000 times their weight in aqueous fluid. SAPs are generally discussed in Goldman et al. U.S. Pat. Nos. 5,669,894 and 5,559,335, and by Mitchell in U.S. Pat. No. 7,249,632, the disclosures of which are incorporated herein by reference. SAPs can differ in their chemical identity, but all SAPs are capable of absorbing and retaining amounts of aqueous fluids equivalent to many times their own weight, even under moderate pressure. For example, SAPs can absorb one hundred times their own weight, or more, of distilled water. The ability to absorb aqueous fluids under a confining pressure is an important requirement for an SAP used in a hygienic article, such as a diaper.

Rebre, in U.S. Pat. Nos. 5,442,014 and 5,373,066, describes the treatment of a certain superabsorbent polymer ("SAP") with hydrogen peroxide during its manufacture. Treatment with hydrogen peroxide apparently reduces the residual monomer content in the SAP product to an acceptable level. The amount of hydrogen peroxide is from 0.08% to 0.19% by weight relative to the dry SAP polymer.

Metal peroxides, or complexes of metallic salts and hydrogen peroxide ("HP"), have been mentioned as antimicrobial treatments for textiles. These compositions may be formed by the reaction of metal salts such as zinc acetate, with hydrogen peroxide in aqueous solution (U.S. Pat. Nos. 5,656,037; 5,152,996; 4,199,322; and 4,174,418).

The industry of superabsorbents (SAPs) is very often confronted with a need to add other properties to these products in addition to their absorption and retention performance qualities. For example, when the absorbent article in place is impregnated with bodily fluids, in particular urine, it gives off powerful and unpleasant odors, e.g. ammoniacal odors arising from the hydrolysis of urea by the bacterial ureases present on the skin and in the digestive tract. With the aim of eliminating these odors from certain SAP products, certain antiodor additives have been taught. Thus, WO 98/20915 and EP 739 635 describe mixtures containing, respectively, zeolites and borax. U.S. Pat. No. 4,842,593 describes diapers containing SAP with pad agents and a nontoxic, nonirritant and nonvolatile antimicrobial agent which is not incorporated in a non-leachable manner.

SUMMARY OF THE INVENTION

The present invention provides compositions, methods, and articles of manufacture. The compositions, desirably having antimicrobial properties, may be made by treating a superabsorbent polymer ("SAP") with hydrogen peroxide ("HP"). The treatment involves swelling the superabsorbent polymer with an aqueous solution of hydrogen peroxide, followed by drying the polymer. This desirably produces a dried composition which is an antimicrobial superabsorbent polymer with non-leaching antimicrobial properties.

The present invention utilizes the inventors' discovery that hydrogen peroxide seems to remain physically trapped in the dried SAP powders after treatment with HP. This has been substantiated by leaching studies (described below), which show that no antimicrobial effect is leached into solution when the treated powders are placed into an excess of saline solution. However, iodometric titration of the treated SAP materials in aqueous solution indicates the presence of active peroxide. Microorganisms such as bacteria are destroyed upon contact with the treated SAP materials. These observations suggest that HP is sequestered in the treated SAP, and released upon demand (i.e. by contact of the treated SAP with either microorganisms, or reagents that are reactive with the sequestered HP).

The antimicrobial compositions of this invention resulting from the treatment of a superabsorbent polymer with hydrogen peroxide are heat-stable, and have good shelf life.

It is an embodiment of the invention to provide a polymeric composition having sequestered peroxide, produced by treating a superabsorbent polymer with at least 0.005 grams of hydrogen peroxide per gram of superabsorbent polymer, wherein the treatment comprises swelling the superabsorbent polymer with a treatment solution comprising aqueous hydrogen peroxide, followed by drying. In a preferred embodiment of the invention the superabsorbent polymer is treated with 0.005 to 0.2 grams of hydrogen peroxide per gram of superabsorbent polymer. In a more preferred embodiment of the invention, the superabsorbent polymer is treated with 0.01 to 0.15 grams of hydrogen peroxide per gram of superabsorbent polymer. In an even more preferred embodiment of the invention, the superabsorbent polymer is treated with 0.02 to 0.15 grams of hydrogen peroxide per gram of superabsorbent polymer.

It is an embodiment of the invention that the treatment solution further comprises a metal salt, in an amount suitable to treat the superabsorbent polymer with at least 0.02 grams of the metal salt per gram of superabsorbent polymer. Suitable metal salts include zinc, magnesium, silver, copper, and zirconium salts. It is preferred that the metal salt is an acetate salt, such as zinc acetate, zinc acetate dihydrate, magnesium acetate, and zirconium acetate. More preferred are the salts, zinc acetate or magnesium acetate.

It is an embodiment of the invention that the superabsorbent polymer be a carboxylate-containing polymer, a cellulose derivative, a polyacrylamide, or a polydiallyldialkylammonium salt. In a preferred embodiment of the invention the superabsorbent polymer is a carboxylate-containing polymer. In a more preferred embodiment of the invention the carboylate-containing polymer is an acrylic acid-based polymer. The acrylic acid-based polymer can also be a cross-linked hydrophilic sodium salt form of a partially neutralized acrylic acid polymer.

It is an embodiment of the invention that the polymeric composition prepared from the superabsorbent polymers and treatment solutions is superabsorbent.

It is an embodiment of the invention to provide a method of making the above-disclosed polymeric compositions by a process comprising the steps of
   a. swelling a superabsorbent polymer with a treatment solution comprising hydrogen peroxide, and
   b. drying the polymer,
whereby hydrogen peroxide is sequestered within or on the surface of the superabsorbent polymer.

It is an embodiment of the invention to provide an antimicrobial composition produced by treating a superabsorbent polymer with at least 0.005 grams of hydrogen peroxide per gram of superabsorbent polymer, wherein the treatment comprises swelling the superabsorbent polymer with an aqueous treatment solution of hydrogen peroxide, followed by drying, whereby contact with the antimicrobial composition provides at least a 3 log reduction in viable bacteria. In a preferred embodiment of the invention the superabsorbent polymer is treated with 0.005 to 0.2 grams of hydrogen peroxide per gram of superabsorbent polymer. In a more preferred embodiment of this invention, the superabsorbent polymer is treated with 0.01 to 0.15 grams of hydrogen peroxide per gram of superabsorbent polymer. In an even more preferred embodiment of the invention the superabsorbent polymer is treated with 0.02 to 0.15 grams of hydrogen peroxide per gram of superabsorbent polymer.

It is an embodiment of the invention that the treatment solution further comprises a metal salt, in an amount suitable to treat the superabsorbent polymer with at least 0.02 grams of the metal salt per gram of superabsorbent polymer. Suitable metal salts include zinc, magnesium, silver, copper, and zirconium salts. It is preferred that the metal salt is an acetate salt, such as zinc acetate, zinc acetate dihydrate, magnesium acetate, and zirconium acetate. More preferred are the salts, zinc acetate or magnesium acetate.

It is an embodiment of the invention that the superabsorbent polymer is a carboxylate-containing polymer, a cellulose derivative, a polyacrylamide, or a polydiallyldialkylammonium salt. In a preferred embodiment of the invention the superabsorbent polymer is a carboxylate-containing polymer. In a more preferred embodiment of the invention the carboxylate-containing polymer is an acrylic acid-based polymer. The acrylic acid-based polymer can also be a cross-linked hydrophilic sodium salt form of a partially neutralized acrylic acid polymer.

It is an embodiment of the invention that the antimicrobial composition comprise superabsorbent polymer in the form of a powder or granular material. It is an embodiment of the invention that the antimicrobial composition prepared from the superabsorbent polymers and treatment solutions is superabsorbent. It is an embodiment of the invention that the antimicrobial activity of the antimicrobial composition is non-leachable.

It is an embodiment of the invention to provide a bandage, wound dressing, tampon, sanitary napkin, diaper, wipe, incontinence device or garment, food packaging, or medical device, comprising an antimicrobial composition of the invention. It is a preferred embodiment of the invention to provide a method of controlling diaper rash by using a diaper or incontinence garment comprising an antimicrobial composition of the invention.

It is an embodiment of the invention to provide a method of making the above-disclosed superabsorbent antimicrobial compositions by a process comprising the steps of
   a. swelling a superabsorbent polymer with a treatment solution comprising hydrogen peroxide, and
   b. drying the polymer,
whereby a superabsorbent polymer having non-leachable antimicrobial activity is produced.

It is an embodiment of the invention to provide a method of disinfecting an infected liquid to produce a 3-log reduction in viable bacteria contain therein. The method steps comprise contacting the liquid with an antimicrobial composition comprising a superabsorbent polymer treated with a treatment solution comprising peroxide, and optionally a metal salt, and drying the produced antimicrobial composition. In a preferred embodiment of the invention the method reduces or controls odor, infection, microbial rashes, or allergies.

It is an embodiment of the invention that the treatment solution is at least 5 times the weight of the superabsorbent polymer.

It is an aspect of this invention to provide a method of inhibiting the proliferation of microorganisms by using a superabsorbent antimicrobial composition resulting from the treatment of a superabsorbent polymer with hydrogen peroxide, wherein the treatment comprises swelling the superabsorbent polymer with an aqueous solution of hydrogen peroxide, followed by drying of the polymer to produce a superabsorbent antimicrobial composition.

It is an aspect of this invention to provide a method of reducing odor and simultaneously controlling diaper rash by the suppression of bacteria that attack urinary urea with the liberation of ammonia by impregnating the diaper fabric with an effective amount of an antimicrobial composition resulting from the treatment of a superabsorbent polymer with hydrogen peroxide, wherein the treatment comprises swelling the superabsorbent polymer with an aqueous solution of hydrogen peroxide, followed by drying of the polymer.

It is therefore an aspect of the present invention to provide compositions, methods of treatment, and articles of manufacture, wherein there is employed an antimicrobial composition resulting from the treatment of a superabsorbent polymer with hydrogen peroxide, wherein the treatment comprises swelling the superabsorbent polymer with an aqueous solution of hydrogen peroxide, followed by drying of the polymer.

It is also an aspect of the present invention to provide compositions, methods of treatment, and articles of manufacture, wherein there is employed an antimicrobial superabsorbent composition resulting from the treatment of a superabsorbent polymer with hydrogen peroxide, wherein the treatment comprises swelling the superabsorbent polymer with an aqueous solution of hydrogen peroxide, followed by drying of polymer, for the purpose of providing the benefits of odor reduction, control of microbes, and reduction of infection or microbial rashes and allergies.

It is also an aspect of the present invention to provide an antimicrobial superabsorbent composition resulting from the treatment of a cross-linked hydrophilic sodium salt form of a partially neutralized acrylic acid-based polymer with hydrogen peroxide, wherein the treatment comprises swelling the superabsorbent polymer with an aqueous solution of hydrogen peroxide, followed by drying of the polymer.

It is also an aspect of the present invention to provide a method of inhibiting the proliferation of microorganisms by using an antimicrobial superabsorbent composition resulting from the treatment of a cross-linked hydrophilic sodium salt form of a partially neutralized acrylic acid-based polymer with hydrogen peroxide, wherein the treatment comprises swelling the superabsorbent polymer with an aqueous solution of hydrogen peroxide, followed by drying of the polymer.

It is also an aspect of the present invention to provide a method of reducing odor and simultaneously controlling diaper rash by the suppression of bacteria that attack urinary urea with the liberation of ammonia by impregnating a diaper with an effective amount of a composition for controlling the spread of infection, the composition being an antimicrobial superabsorbent composition resulting from the treatment of a cross-linked hydrophilic sodium salt form of a partially neutralized acrylic acid-based polymer with hydrogen peroxide, wherein the treatment comprises swelling the superabsorbent polymer with an aqueous solution of hydrogen peroxide, followed by drying of the polymer.

It is therefore an aspect of the present invention to provide compositions, methods of treatment, and articles of manufacture, wherein there is employed an antimicrobial superabsorbent composition resulting from the treatment of a cross-linked hydrophilic sodium salt form of a partially neutralized acrylic acid-based polymer with hydrogen peroxide, wherein the treatment comprises swelling the superabsorbent polymer with an aqueous solution of hydrogen peroxide, followed by drying of the polymer.

It is also an aspect of the present invention to provide compositions, methods of treatment, and articles of manufacture, wherein there is employed an antimicrobial superabsorbent composition resulting from the treatment of a cross-linked hydrophilic sodium salt form of a partially neutralized acrylic acid-based polymer with hydrogen peroxide, wherein the treatment comprises swelling the superabsorbent polymer with an aqueous solution of hydrogen peroxide, followed by drying of the polymer, for the purpose of providing the benefits of odor reduction, control of microbes, and reduction of infection or microbial rashes and allergies.

It is also an aspect of the present invention to provide a method of inhibiting the proliferation of microorganisms by using an antimicrobial superabsorbent composition resulting from the treatment of a cross-linked hydrophilic sodium salt form of a superabsorbent polymer with hydrogen peroxide and optionally, a metal salt, wherein the treatment comprises swelling the superabsorbent polymer with an aqueous solution of hydrogen peroxide and metal salt, followed by drying of the polymer.

It is also an aspect of the present invention to provide a method of reducing odor and simultaneously controlling diaper rash by the suppression of bacteria that attack urinary urea with the liberation of ammonia by impregnating a diaper with an effective amount of a composition for controlling the spread of infection, the composition being an antimicrobial superabsorbent composition resulting from the treatment of a superabsorbent polymer with hydrogen peroxide and optionally, a metal salt, wherein the treatment comprises swelling the superabsorbent polymer with an aqueous solution of hydrogen peroxide and metal salt, followed by drying of the polymer.

It is therefore an aspect of the present invention to provide compositions, methods of treatment, and articles of manufacture, wherein there is employed an antimicrobial superabsorbent composition resulting from the treatment of a superabsorbent polymer with hydrogen peroxide and optionally, a metal salt, wherein the treatment comprises swelling the superabsorbent polymer with an aqueous solution of hydrogen peroxide and metal salt, followed by drying of the polymer.

It is also an aspect of the present invention to provide compositions, methods of treatment, and articles of manufacture, wherein there is employed an antimicrobial superabsorbent composition resulting from the treatment of a superabsorbent polymer with hydrogen peroxide and optionally, a metal salt, wherein the treatment comprises swelling the superabsorbent polymer with an aqueous solution of hydrogen peroxide and metal salt, followed by drying of the polymer, for the purpose of providing the benefits of odor reduction, control of microbes, and reduction of infection or microbial rashes and allergies.

It is also an aspect of the present invention to provide an antimicrobial superabsorbent composition resulting from the treatment of a cross-linked hydrophilic sodium salt form of a partially neutralized acrylic acid-based polymer with hydrogen peroxide and optionally, a metal salt, wherein the treatment comprises swelling the superabsorbent polymer with an aqueous solution of hydrogen peroxide and metal salt, followed by drying of the polymer.

It is also an aspect of the present invention to provide a method of inhibiting the proliferation of microorganisms by using an antimicrobial superabsorbent composition resulting from the treatment of a cross-linked hydrophilic sodium salt form of a partially neutralized acrylic acid-based polymer with hydrogen peroxide and optionally, a metal salt, wherein the treatment comprises swelling the superabsorbent polymer with an aqueous solution of hydrogen peroxide and metal salt, followed by drying of the polymer.

It is also an aspect of the present invention to provide a method of reducing odor and simultaneously controlling diaper rash by the suppression of bacteria that attack urinary urea with the liberation of ammonia by impregnating the diaper with an effective amount of a composition for controlling the spread of infection, the composition being an antimicrobial superabsorbent composition resulting from the treatment of a cross-linked hydrophilic sodium salt form of a partially neutralized acrylic acid-based polymer with hydrogen peroxide and optionally, a metal salt, wherein the treatment comprises swelling the superabsorbent polymer with an aqueous solution of hydrogen peroxide and metal salt, followed by drying of the polymer.

It is therefore an aspect of the present invention to provide compositions, methods of treatment, and articles of manufacture, wherein there is employed an antimicrobial superabsorbent composition resulting from the treatment of a cross-linked hydrophilic sodium salt form of a partially neutralized acrylic acid-based polymer with hydrogen peroxide and optionally, a metal salt, wherein the treatment comprises swelling the superabsorbent polymer with an aqueous solution of hydrogen peroxide and metal salt, followed by drying of the polymer.

It is also an aspect of the present invention to provide compositions, methods of treatment, and articles of manufacture, wherein there is employed an antimicrobial superabsorbent composition resulting from the treatment of a cross-linked hydrophilic sodium salt form of a partially neutralized acrylic acid-based polymer with hydrogen peroxide and optionally, a metal salt, wherein the treatment comprises swelling the superabsorbent polymer with an aqueous solution of hydrogen peroxide and metal salt, followed by drying of the polymer, for the purpose of providing the benefits of odor reduction, control of microbes, and reduction of infection or microbial rashes and allergies.

In an embodiment of this invention a superabsorbent polymer is treated with an aqueous treatment solution.

It is an advantage of this invention that a strong or mineral acid is not required to catalyze the reaction of the SAP with hydrogen peroxide in order to form a superabsorbent antimicrobial composition.

It is an embodiment of this invention that the superabsorbent material be dried immediately after swelling of the superabsorbent polymer with the treatment solution.

In an embodiment of this invention the superabsorbent material is stored after swelling with the treatment solution for a predetermined length of time at a predetermined temperature before drying, in order to allow the treatment solution to react with the polymer.

In a preferred embodiment of this invention, the superabsorbent polymer is a cross-linked hydrophilic sodium salt form of a partially neutralized acrylic acid-based polymer.

In an embodiment of this invention, enough treatment solution is applied to uniformly wet the superabsorbent polymer.

In an embodiment of this invention the minimum amount of treatment solution is applied which results in uniform wetting of the superabsorbent polymer, as this requires the least energy input to effect drying of the treated material. It is not necessary that the superabsorbent polymer absorb the entire treatment solution which is applied.

In an embodiment of this invention the treatment solutions comprising aqueous hydrogen peroxide and metal salts further comprise an acid added to enhance solubility of the metal salt and hydrogen peroxide mixture in the aqueous treatment solution. A preferred acid for this purpose is acetic acid.

In an embodiment of this invention, at least 0.02 grams of metal salt per gram of superabsorbent polymer is used; in a more preferred embodiment of this invention at least 0.05 grams of metal salt per gram of superabsorbent polymer is used; and in a most preferred embodiment, at least 0.10 grams of metal salt per gram of superabsorbent polymer is used.

It is an aspect of this invention that after treatment of the superabsorbent material with the treatment solution, the treated material be dried.

DETAILED DESCRIPTION OF THE INVENTION

Definitions

Figure 1:
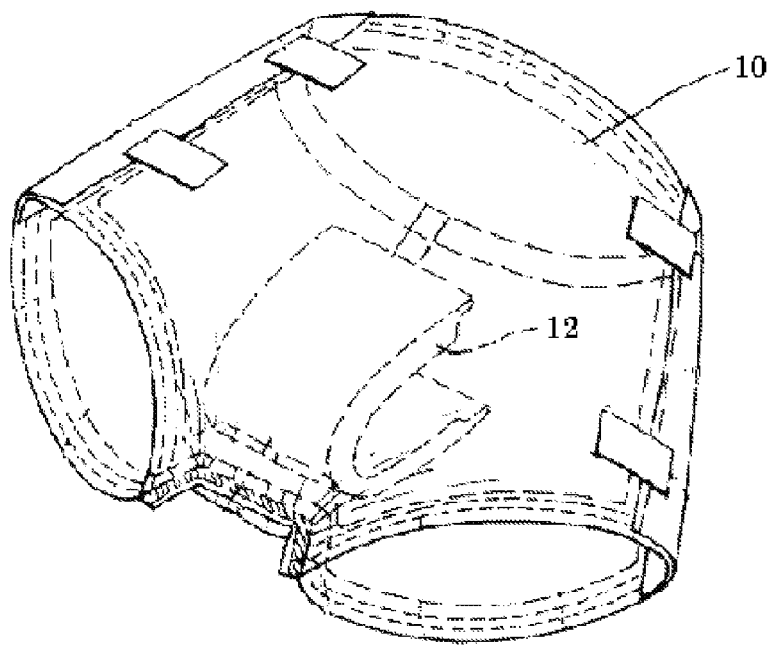
FIG. 1 shows a diaper in accordance with the present invention.

"Microbe" or "microorganism" refers to any organism or combination of organisms such as bacteria, viruses, protozoa, yeasts, fungi, molds, or spores formed by any of these.

"Antimicrobial" refers to the microbicidal or microbistatic properties of a compound, composition, article, or material that enables it to kill, destroy, inactivate, or neutralize a microorganism; or to prevent or reduce the growth, ability to survive, or propagation of a microorganism.

"Substrate" refers to a surface or medium upon which an antimicrobial, such as a peroxide, is chemically bonded. Alternatively, a substrate is a surface, object, or material which is reacted with a reagent, such as hydrogen peroxide, to produce an antimicrobial composition, or antimicrobially-modified substrate. In the case of the present invention, the substrate is a superabsorbent polymer.

"Surface" refers to the common outside surface of the substrate (a superabsorbent polymer in this case), and also to the internal surfaces of voids, channels, or pores within the substrate.

By "inherently antimicrobial" is meant a property of a material wherein the material would exhibit antimicrobial activity or properties in the absence of any antimicrobial activity or properties contributed by agents, compounds, or additives which are not integral to the material, not chemically bonded to the material, or detachable from the material, or after the removal or depletion of such agents, compounds, or additives from the material. "Inherently antimicrobial" does not mean that the material contains no leachable agents with antimicrobial activity.

By "non-leaching" is meant that the antimicrobial peroxides of the present invention, once attached to the material or substrate via the method of the current invention, do not appreciably separate from, migrate out of, or away from the material or substrate, enter a wound, or otherwise become non-integral with the material or substrate under standard uses. By "not appreciably separate" is meant that no more than an insubstantial amount of antimicrobial peroxide separates, for example less than one percent, preferably less than 0.1 percent, more preferably less than 0.01 percent, and even more preferably less than 0.001 percent of the total quantity of antimicrobial peroxide. Alternatively, "not appreciably separate" means that the solution concentration of antimicrobial peroxide resulting from separation of attached antimicrobial peroxide, in a liquid in contact with the material or substrate, does not exceed a predetermined level, for example less than 0.01%, preferably less than 0.005%, and more preferably less than 0.001%. Alternately, depending on the application, "not appreciably separate" may mean that no adverse effect on wound healing or the health of an adjacent tissue of interest is measurable. It should be understood that particular definition may depend on the application in which the invention is used. For medical applications such as wound dressings, the overriding concern would be to ensure that the localized concentration of leachable material remains below a specific level at a given point in time, or leads to no adverse effects over the period of use.

A non-leaching antimicrobial composition may be classified as "inherently antimicrobial", in that the composition possesses antimicrobial properties without the addition of a separate antimicrobial agent. Generally, the term non-leaching would be applied only to a solid composition. Non-leaching properties manifest two distinct benefits. First, the level of antimicrobial in the composition is not reduced or diluted by contact with fluids. In other words, the antimicrobial cannot be washed-out and depleted. Second, the antimicrobial will remain bound to the composition and not be transferred to the surrounding environment, where it may have undesirable effects. An example is a wound dressing, where leaching of antimicrobial into the wound might cause cellular toxicity or interfere with healing.

By "superabsorbent polymer", or "SAP", is meant a polymeric material that imbibes or absorbs at least 10 times its own dry weight in aqueous fluid and that retains the imbibed or absorbed aqueous fluid under moderate pressure. The imbibed or absorbed aqueous fluid is taken into the SAP rather than being contained in macroscopic pores from which the fluid could be eliminated by squeezing. Examples of SAPs include, but are not limited to acrylate and methacrylate polymers. Goldman et al. (U.S. Pat. Nos. 5,669,894 and 5,559,335) and Mitchell (U.S. Pat. No. 7,249,632) generally discuss superabsorbent polymers. The disclosures of these patents are incorporated by reference herein except where inconsistent with the present disclosure.

"Acrylic acid-based polymer" means a polymer formed by the polymerization of acrylic acid or a derivative thereof such as methacrylic acid, or, alternatively, the fully- or partially-neutralized salts of such a polymer. The acrylic acid-based polymer may be crosslinked and/or may be hydrophilic.

As used herein, the term "SAP particles" refers to superabsorbent polymer particles in the dry state, i.e., particles containing from no water up to an amount of water less than the weight of the dry particles. The term "particles" refers to granules, fibers, flakes, spheres, powders, platelets, and other shapes and forms known to persons skilled in the art of superabsorbent polymers. The terms "SAP gel" and "SAP hydrogel" refer to a superabsorbent polymer in the hydrated state, i.e., particles that have absorbed at least their weight in water, and typically several times their weight in water. The term "surface crosslinking" means that the level of functional crosslinks in the SAP particle in the vicinity of the surface of the particle is generally higher than the level of functional crosslinks in the SAP particle in the interior of the particle. The term "surface-crosslinked SAP particle" refers to an SAP particle having its molecular chains present in the vicinity of the particle surface cross-linked by a compound applied to the surface of the particle.

Initially, the swelling capacity of an SAP particle on contact with liquids, also referred to as free swelling capacity, was the main factor in the design and development of SAP particles. Later, however, it was found that not only is the amount of absorbed liquid important, but the stability of the swollen gel, or gel strength, also is important. The free swelling capacity on one hand, and the gel strength on the other hand, represent contrary properties. Accordingly, SAP particles having a particularly high absorbency typically exhibit a poor gel strength, such that the gel deforms under pressure (e.g., the load of a body), and prevents further liquid distribution and absorption.

A balanced relation between absorptivity (gel volume) and gel strength is desired to provide proper liquid absorption, liquid transport, and dryness of a diaper and the skin when using SAP particles in a diaper. In this regard, not only is the ability of SAP particles to retain a liquid under subsequent pressure an important property, but absorption of a liquid against a simultaneously acting pressure, i.e., during liquid absorption also is important. This is the case in practice when a child or adult sits or lies on a sanitary article, or when shear forces are acting on the sanitary article, e.g., leg movements. This absorption property is referred to as absorption under load.

Investigators have researched various methods of improving the amount of liquid absorbed and retained by SAP particles, especially under load, and the rate at which the liquid is absorbed. One preferred method of improving the absorption and retention properties of SAP particles is to surface crosslink the SAP particles.

As understood in the art, surface-crosslinked SAP particles have a higher level of crosslinking in the vicinity of the surface than in the interior. As used herein, "surface" describes the outer-facing boundaries of the particle. For porous SAP particles, exposed internal surface also are included in the definition of surface.

Absorbent polymers capable of absorbing from about thirty to sixty grams of water per gram of polymer are known, as is the use of such polymers in disposable diapers, sanitary napkins, surgical pads, and bath mats, for example. Particularly sought-after property is increased water absorbency. Polymers having this property often are referred to as hydrogels or superabsorbents. The nature and utility of superabsorbents are illustrated by U.S. Pat. No. 4,449,977. According to this reference, a desirable feature of a superabsorbent is the presence of acrylate or methacrylate groups which can be salts, amides, esters, or the free acids. Many hydrogels are based on acrylate and methacrylate polymers and copolymers, for example, as shown in U.S. Pat. Nos. 2,976,576, 3,220,960, 3,993,616, 4,154,898, 4,167,464, 4,192,727, 4,192,827, and 4,529,739. Hydrogels based on starch or a modified starch are shown by U.S. Pat. Nos. 4,069,177, 4,076,663, 4,115,332, and 4,117,222. Other hydrogels are based on poly(oxyalkylene)glycols as in U.S. Pat. No. 3,783,872. Hydrogels prepared from hydrolyzed crosslinked polyacrylamides and crosslinked sulfonated polystyrenes are described in U.S. Pat. No. 4,235,237. Finally, polymers based on maleic anhydride are described in U.S. Pat. Nos. 2,988,539, 3,393,168, 3,514,419, 3,557, 067, and 4,401,793. U.S. Pat. No. 3,900,378 describes hydrogels from radiation crosslinked blends of hydrophilic polymers and fillers. Such category of absorbent polymers preferred in the present invention, however, can be exemplified by, for example, U.S. Pat. No. 3,966,679, which relates to acrylic acid-based water-swellable superabsorbent polymers useful as catamenial tampons and diapers.

Hydrogen peroxide is favored in many applications because its breakdown products, water and oxygen, are innocuous, and it tends to have broad spectrum antimicrobial activity. Broad spectrum activity is important in situations where harmful organisms are present but their identity is not known. Hydrogen peroxide is a well known antiseptic which has been extensively employed in aqueous solution for the treatment of infectious processes in both human and veterinary topical therapy. The agent can be used in its original form after suitable dilution, or it can be derived from those solid compounds which form salts or additive compounds with hydrogen peroxide. Included among these are sodium perborate, sodium carbonate peroxide, sodium peroxyphosphate, urea peroxide, potassium persulfate, and others. When added to water, these compounds hydrolyze into hydrogen peroxide and the corresponding carrying salt. The principal limitations of commonly used peroxide aqueous solutions, however, are their poor shelf stability caused by the decomposition of hydrogen peroxide into gaseous oxygen and water at room temperature, and the transitory contact of the active oxygenating agent with the affected tissue. In addition, when such compositions are formed of additive compounds with hydrogen peroxide, it is common to prepare the adduct composition before incorporating it into the desired composition.

Blank, in U.S. Pat. Nos. 4,985,023, 4,990,338, 5,035,892, 5,045,322, 5,061,487, and 5,079,004 describes an antimicrobial superabsorbent composition of a cross-linked hydrophilic sodium salt form of a partially neutralized acrylic acid-based polymer gel having covalently bonded thereto a silane quaternary ammonium antimicrobial. The composition can be in the form of flakes, strips, powders, filaments, fibers, or films, and may be applied to a substrate in the form of a coating. Quaternary ammonium antimicrobials are known to be very effective against many types of bacteria; however, they are generally less effective against spores, fungi, and viruses.

Hobson, in U.S. Pat. No. 6,399,092 describes an anhydrous, hydrophilic wound dressing containing a superabsorbent polymer and an antimicrobial agent. Its anhydrous nature allows it, when applied to a wound site, to absorb wound fluid and slowly release its water-soluble active microbial agent into the wound.

Each of the above-mentioned U.S. patents and U.S. patent applications is hereby incorporated by reference except where inconsistent with the technical disclosure herein.

DETAILED DESCRIPTION

The present invention includes an antimicrobial composition resulting from the treatment of a superabsorbent polymer (SAP) with a treatment solution comprising hydrogen peroxide (HP). The treatment includes the steps of swelling the superabsorbent polymer with an aqueous solution of hydrogen peroxide followed by drying of the polymer, whereby the dried composition is an antimicrobial superabsorbent polymer with non-leaching antimicrobial properties. The antimicrobial composition can optionally comprise a metal ion.

The antimicrobial compositions may be prepared by the processes disclosed herein. Commercially-available SAPs are treated with a treatment solution comprising hydrogen peroxide (HP). The SAP is allowed to absorb aqueous solutions of HP for a length of time that allows the HP solution to swell. The absorption step may be carried out at room temperature. Alternatively, higher or lower temperatures are suitable for swelling the SAP. The treated SAP may be immediately dried or stored for a predetermined length of time at a predetermined temperature before drying. Any temperature and time combination that results in thorough drying of the treated SAP may be used. One skilled in the art will recognize that drying conditions may affect the absorbance properties (rate and extent) of the finished antimicrobial SAP product, and will employ appropriate conditions to assure optimization of these properties, if necessary.

The inventors discovered that materials treated in this manner maintained a residual antimicrobial capacity even after drying. We expected that HP would be completely removed from the SAP substrate by drying because it is relatively volatile. However, a significant amount of antimicrobial effect was observed for the dried SAP materials after treatment with HP. It is believed that the antimicrobial effect exhibited by the dried SAP powder after treatment with HP is a result of reaction between carboxylate groups of the SAP and hydrogen peroxide to form peracids (also known as peroxyacid or percarboxylic) groups, or the sodium salts thereof. However, such reactions normally require catalysts (such as a strong mineral acid), whereas on the contrary, no such catalyst is required in order to realize the residual antimicrobial effect in the products of the current invention. Alternatively, HP is otherwise sequestered or bound in the treated SAP in a nonvolatile and non-leaching manner, and HP becomes available on demand for oxidative reaction, or to function as an antimicrobial. The SAP, after treatment or reaction with HP, followed by drying, is able to provide a controlled-release, sustained-release, or on-demand-release of chemical and biochemical properties normally associated with HP.

Antimicrobial compositions comprising metal salts can be prepared by a variation of the general procedure immediately above. Certain metal salts (zinc acetate, for example) can be combined with HP in a treatment solution and used to treat a SAP material in order to impart antimicrobial properties to the SAP. In a typical procedure commercially available SAPs are allowed to absorb aqueous solutions of HP and the metal salt, followed by drying of the treated SAP materials. In some cases, the combination of HP and metal salt provides an enhancement of antimicrobial effect compared to HP alone; however, it is found that the major contribution to antimicrobial effectiveness is due to the HP component, not the metal salt.

The inventors have prepared zinc-containing antimicrobial superabsorbent polymers (SAPs) via a process wherein a solution of zinc salts mixed with hydrogen peroxide (HP) is combined with a preformed SAP. Suitable zinc salts include zinc peroxide, zinc oxide, and zinc acetate (ZA). The SAP was allowed to absorb the solutions and then dried. The process forms and traps metal peroxides or polymeric complexes derived from zinc peroxide, zinc oxide, and zinc acetate within, and on the surface of, the SAP powder particles in order to produce a non-leaching antimicrobial superabsorbent composition.

In order to investigate the effect of different variables, (such as reagent combinations, ratios, and concentrations) experiments were performed using either zinc acetate combined with HP, zinc acetate alone (no HP), or hydrogen peroxide alone (no ZA). It is completely unexpected that any residual antimicrobial effect would be seen from SAP powders treated only with hydrogen peroxide, as HP is volatile, and should be completely removed form the substrate when it is dried. Surprisingly, a significant amount of antimicrobial effect was observed even for the SAP materials treated with only HP (in the absence of zinc salts), and this effect was several orders of magnitude higher than for the material prepared with only zinc acetate. It is presumed that the antimicrobial effect exhibited by the dried SAP powder after treatment with hydrogen peroxide is a result of reaction between carboxylate groups of the SAP and hydrogen peroxide to form peracids (also known as peroxyacid or percarboxylic) groups, or the sodium salts thereof. Alternatively, HP may be otherwise sequestered in the treated SAP in a nonvolatile and non-leaching manner, and available on demand for oxidative reaction, or to function as an antimicrobial.

In the above-mentioned experiments, SAP materials (crosslinked sodium polyacrylate powders) treated with a treatment solution comprising zinc acetate and HP exhibited significant antimicrobial activity, showing a 6.2 log reduction (full kill) when placed into 50 times their weight of phosphate buffered saline containing approximately 1,000,000 cfu/mL of $E.\ Coli$. When HP was omitted (zinc acetate only), the antimicrobial activity decreased by a factor of more than 10,000 (only 1.8 log reduction). Surprisingly, when zinc acetate was omitted (HP-only), the antimicrobial activity remained very high (5.6 log reduction, or higher in some cases).

It is known in the art to use strong mineral acids to catalyze the reaction between hydrogen peroxide and a carboxylic acid in order to form a peracid. However, it was found that such acid catalysts are not required for the formation of useful antimicrobial superabsorbent compositions via the reaction of a superabsorbent polymer and hydrogen peroxide. Indeed, most commercial SAP compositions are formulated to not give an acidic pH when exposed to water, as the absorbent capacity of a carboxylate-based SAP is reduced at low pH. This may mean that the formation of peracid does not result from treatment of the SAP with HP. Regardless, antimicrobial activity is observed even after the treated SAP substrate is dried. A complete understanding of the exact chemical reactions and chemical species involved in this process is not necessary to enable a person having ordinary skill in the art to practice the invention.

It is an embodiment of the present invention to provide compositions, methods of treatment, and articles of manufacture, wherein there is employed an antimicrobial superabsorbent composition resulting from the treatment of a cross-linked hydrophilic sodium salt form of a partially neutralized acrylic acid-based polymer with hydrogen peroxide. The treatment comprises swelling the superabsorbent polymer with an aqueous treatment solution comprising hydrogen peroxide, followed by drying of polymer, to produce a superabsorbent antimicrobial composition for the purpose of providing the benefits of odor reduction, control of microbes, and reduction of infection or microbial rashes and allergies.

It is also an embodiment of the present invention to provide compositions, methods of treatment, and articles of manufacture, wherein there is employed an antimicrobial superabsorbent composition resulting from the treatment of a superabsorbent polymer with hydrogen peroxide and optionally, a metal salt, wherein the treatment comprises swelling the superabsorbent polymer with an aqueous treatment solution comprising hydrogen peroxide and metal salt, followed by drying of the polymer to produce a superabsorbent antimicrobial composition.

In preferred embodiments of the aspects of the invention, the metal salt is chosen from the group comprising; salts of zirconium, zinc, copper, silver, or magnesium. In a more preferred embodiment, the metal salt is a zinc or magnesium salt. In a preferred embodiment of this invention, the metal salt is an acetate salt. In a most preferred embodiment of this invention, the metal salt is zinc acetate or magnesium acetate.

Superabsorbent polymer materials suitable for the practice of this invention include those which are soluble, insoluble, gels, powders, films, coatings, complexes, copolymers, fibers, etc. Exemplifying superabsorbent polymer materials useful in the practice of this invention include carboxylate-containing polymer for example, polyacrylates, polymethacrylates, alginates, cellulose derivatives such as carboxymethylcellulose, polylactides, polyglycolides, polysaccharides, or any polymer containing a carboxylate group. Other superabsorbent polymers such as those comprising polyacrylamides and polydiallyldialkylammonium salts, such as polyDADMAC are also suitable for the practice of this invention. The polymers may optionally have quaternary ammonium groups attached thereto.

In one embodiment of this invention, the superabsorbent polymer is in the form of a powder or granular material. In a preferred embodiment of this invention, the superabsorbent polymer is a cross-linked hydrophilic sodium salt form of a partially neutralized acrylic acid-based polymer.

The antimicrobial superabsorbent compositions of the invention are useful for reducing urinary odors, controlling diaper rash, reducing the proliferation of microorganisms, reducing of infection, microbial rashes, and allergies.

The antimicrobial compositions of this invention resulting from the treatment of a superabsorbent polymer with hydrogen peroxide are heat-stable, and do not lose potency after storage for several months.

After treatment of the superabsorbent material with hydrogen peroxide, the treated material is dried. One skilled in the art will recognize that drying conditions may affect the absorbance properties (rate and extent) of the finished antimicrobial SAP product, and will employ appropriate conditions to assure optimization of these properties, if necessary.

One method of preparing the superabsorbent antimicrobial composition comprises the steps treating the a superabsorbent polymer with hydrogen peroxide, wherein the treatment comprises swelling the superabsorbent polymer with an aqueous solution of hydrogen peroxide, followed by drying of the polymer to produce a superabsorbent antimicrobial composition. The resulting superabsorbent antimicrobial composition inhibits the proliferation of microorganisms When diaper fabric is treated with an effective amount of an antimicrobial composition produced by the above described method, suppression of bacteria that attack urinary urea with the liberation of ammonia occurs resulting in a reduction in odors and control of diaper rash. Similarly, when articles of manufacture are prepared from components comprising an antimicrobial superabsorbent composition of this invention, the resulting article receives the benefits of odor reduction, control of microbes, and reduction of infection or microbial rashes and allergies.

Compositions, methods of treatment, and articles of manufacture comprising a cross-linked acrylic acid-based polymer are within the scope of this invention. For example, an antimicrobial superabsorbent composition also results from the treatment of a cross-linked hydrophilic sodium salt form of a partially neutralized acrylic acid-based polymer with hydrogen peroxide, wherein the treatment comprises swelling the superabsorbent polymer with an aqueous solution of hydrogen peroxide, followed by drying of the polymer. Such an antimicrobial superabsorbent composition inhibits the proliferation of microorganisms. It also reduces odor, and controls diaper rash by suppressing bacteria that attack urinary urea with the liberation of ammonia. The compositions or the articles of manufacture comprising the antimicrobial composition provide the benefits of odor reduction, control of microbes, and reduction of infection or microbial rashes and allergies.

The antimicrobial superabsorbent composition may optionally comprise a metal salt. Such a composition is prepared by swelling the superabsorbent polymer with an aqueous solution of hydrogen peroxide and metal salt, followed by drying of the polymer. The resulting composition may be used to provide methods of treatment, for example, a method of inhibiting the proliferation of microorganisms, reducing odor, or controlling diaper rash by suppressing bacteria that attack urinary urea with the liberation of ammonia. Articles of manufacture can be prepared from components comprising the antimicrobial superabsorbent composition and optionally comprising a metal salt.

An antimicrobial superabsorbent composition of the invention may comprise a cross-linked hydrophilic sodium salt form of a partially neutralized acrylic acid-based polymer and a metal salt. Such a composition may be prepared by treating a cross-linked hydrophilic sodium salt form of a partially neutralized acrylic acid-based polymer with hydrogen peroxide and a metal salt, wherein the treatment comprises swelling the superabsorbent polymer with an aqueous solution of hydrogen peroxide and metal salt, followed by drying of the polymer. The antimicrobial superabsorbent composition so prepared may be used to provide methods of treatment, for example, a method of inhibiting the proliferation of microorganisms.

As a specific example, one of ordinary skill in the art may reduce odor of a diaper and simultaneously control diaper rash by impregnating the diaper with an effective amount of a composition for controlling the spread of infection. The antimicrobial composition in the treated diaper suppresses bacteria that attack urinary urea with the liberation of ammonia. Thus the antimicrobial compositions of the invention provide the benefits of odor reduction, control of microbes, and reduction of infection or microbial rashes and allergies. Articles of manufacture can be prepared from the antimicrobial superabsorbent composition resulting from the treatment of a cross-linked hydrophilic sodium salt form of a partially neutralized acrylic acid-based polymer with hydrogen peroxide and a metal salt.

In an embodiment of this invention, the superabsorbent material is stored after swelling with the treatment solution for a predetermined length of time at a predetermined temperature before drying, in order to allow the treatment solution to react with the polymer.

In a preferred embodiment of this invention, enough treatment solution is applied to uniformly wet the superabsorbent polymer.

In a preferred embodiment of this invention the minimum amount of treatment solution is applied which results in uniform wetting of the superabsorbent polymer, as this requires the least energy input to effect drying of the treated material. It is not necessary that the superabsorbent polymer absorb the entire treatment solution which is applied.

In a preferred embodiment of this invention, the superabsorbent polymer is treated with at least 5 times it weight of treatment solution.

In a preferred embodiment of this invention the treatment solution comprises aqueous hydrogen peroxide.

In another embodiment of this invention, the treatment solution comprises aqueous hydrogen peroxide and a metal salt.

In a more preferred embodiment of this invention, the treatment solution comprises aqueous hydrogen peroxide and zinc acetate or hydrogen peroxide and magnesium acetate.

In an embodiment of this invention the treatment solutions comprising aqueous hydrogen peroxide and metal salts further comprise an acid added to enhance solubility of the metal salt and hydrogen peroxide mixture in the aqueous treatment solution. A preferred acid for this purpose is acetic acid.

In an embodiment of this invention, at least 0.005 grams hydrogen peroxide per gram of superabsorbent polymer is used. In a preferred embodiment of this invention, at least 0.02 grams hydrogen peroxide per gram of superabsorbent polymer is used; in a more preferred embodiment of this invention at least 0.05 grams hydrogen peroxide per gram of superabsorbent polymer is used; and in a most preferred embodiment, at least 0.10 grams hydrogen peroxide per gram of superabsorbent polymer is used.

In a preferred embodiment of this invention, at least 0.02 grams of metal salt per gram of superabsorbent polymer is used; in a more preferred embodiment of this invention at least 0.05 grams of metal salt per gram of superabsorbent polymer is used; and in a most preferred embodiment, at least 0.10 grams of metal salt per gram of superabsorbent polymer is used.

It is an embodiment of this invention that after treatment of the superabsorbent material with the treatment solution, the treated material is dried. One skilled in the art will recognize that drying conditions may affect the absorbance properties (rate and extent) of the finished antimicrobial SAP product, and will employ appropriate conditions to assure optimization of these properties, if necessary.

Superabsorbent materials useful in the practice of this invention include those which are soluble, insoluble, gels, powders, films, coatings, complexes, copolymers, fibers, etc. Superabsorbent materials useful in the practice of this invention include carboxylate-containing polymer for example, polyacrylates, polymethacrylates, alginates, cellulose derivatives such as carboxymethylcellulose, polylactides, polyglycolides, polysaccharides, or any polymer containing a carboxylate group.

It is an embodiment of this invention to provide a method of disinfecting a liquid to produce a 3-log reduction in viable bacteria in the liquid, which comprises mixing the liquid with an antimicrobial composition resulting from the treatment of a superabsorbent polymer with hydrogen peroxide, wherein the treatment comprises swelling the superabsorbent polymer with an aqueous solution of hydrogen peroxide, followed by drying of the polymer.

Numerous articles may be made of the antimicrobial SAP compositions of the present invention. For example, an article of manufacture of the present invention includes a bandage, wound dressing, tampon, sanitary napkin, diaper, wipe, incontinence device or garment, food packaging, medical device, or other application where an antimicrobial SAP would provide benefit.

As alternative embodiments of this invention, organic and inorganic peroxides may be employed in the practice of this invention instead of hydrogen peroxide. Examples include: sodium peroxide, perborates, persulfates, sodium carbonate peroxide, sodium peroxyphosphate, urea peroxide, benzoyl peroxide, t-butylhydroperoxide, and the like, which may be employed in various forms, such as neat, solutions, dispersions, suspensions, and the like.

In embodiment of this invention the dried antimicrobial superabsorbent material is capable of effecting a reduction of viable bacteria when 0.2 grams of the composition is added to approximately 11 mL of aqueous liquid which contains approximately 1,000,000 viable bacterial organisms. In a preferred embodiment of this invention, the reduction of viable bacteria is such that less than 1,000 viable organisms remain (3-log reduction). In a more preferred embodiment of this invention, the reduction of viable bacteria is such that less than 100 viable organisms remain (4-log reduction). In an even more preferred embodiment of this invention, the reduction of viable bacteria is such less than 10 viable organisms remain (5-log reduction). In a most preferred embodiment of this invention, the reduction is such that zero viable organisms remain (6-log reduction, or full-kill). In a preferred embodiment of this invention, the reduction of viable bacteria occurs within 24 hours. In a more preferred embodiment of this invention, the reduction of viable bacteria occurs in less than 10 hours. In a still more preferred embodiment of this invention, the reduction of viable bacteria occurs in less than 4 hours. In a still more preferred embodiment of this invention, the reduction of viable bacteria occurs in less than 2 hours. In an even more preferred embodiment of this invention, the reduction of viable bacteria occurs in less than 1 hour. In the most preferred embodiment of this invention, the reduction of viable bacteria occurs in less than 30 minutes.

It is an aspect of the inventive method to use any temperature and time combination that results in thorough drying of the material. As used herein, thoroughly dried means, for instance, that a substrate exposed to a solution of hydrogen peroxide is then dried to a constant weight. As used herein, dried to a constant weight means dried to the point at which continued application of the chosen drying procedure will no longer result in a considerable additional measurable loss of weight due to evaporation of water or other solvent. Attainment of constant weight is a useful tool to measure extent of dryness; however, the attainment of constant weight is not the actual factor that enables non-leachable attachment of the antimicrobial to the substrate. The particular temperatures and drying times necessary to achieve thorough drying depend, among other things, on the particular substrate material, the initial amount of moisture in the article, the weight and size of the article, the amount of airflow provided to the article during drying, and the humidity of the air or other medium contacting the article. Any drying apparatus, drying method, and temperature and drying time combination that thoroughly dries the treated substrate is sufficient. For purposes of illustration, depending on the particular characteristics of a particular application, the drying step may be performed in an oven (e.g. 80° C. for 2 hours), in a high throughput furnace (e.g. 140° C. for 30 seconds), in a clothes dryer, in a desiccator, in a vacuum chamber, in a dehumidifier, in a dehydrator, or in a lyophilizer (freeze dryer). Infrared heat, radiant heat, microwaves, and hot air are all suitable drying methods for the substrate which has been exposed to the treatment solution. The upper limit of drying temperature for a particular application will generally be determined by the degradation temperature of the particular substrate or peroxide. Other drying methods such as supercritical fluid drying may also be successfully employed in the practice of this invention. Freeze drying may be used.

In the appended drawings, FIG. 1 shows a diaper 10, comprising an absorbent pad 12 used to contain urine and other bodily wastes.

Figure 2:
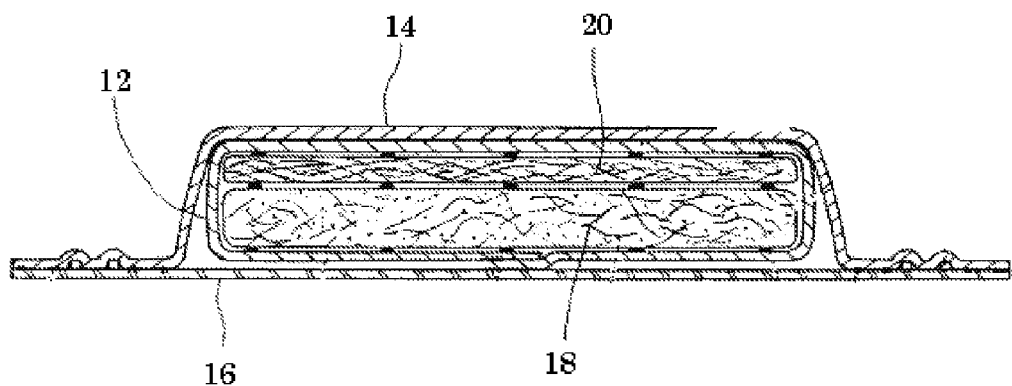
FIG. 2 is a cross-sectional view of the absorbent pad 1 shown in FIG. 1.

As shown in cross-section in FIG. 2, the pad 12 contains a top sheet 14 and a back sheet 16. The liquid-absorbing layer 18 consists essentially of an antimicrobial composition as disclosed herein, comprising a superabsorbent polymer, hydrogen peroxide, and optionally, a metal salt. Above the liquid-absorbing layer is a layer 20 containing fluff pulp for comfort of the wearer.

EXAMPLES

Example 1: Treatment of an Acrylate SAP with Zinc Acetate and Hydrogen Peroxide (Sample ZNP-1)

Twenty grams of an SAP powder (cross-linked hydrophilic sodium salt form of a partially neutralized acrylic acid-based polymer, similar to Luquasorb or HySorb materials manufactured by BASF) was added to a solution prepared by dissolving 4 grams of zinc acetate dihydrate (Aldrich Chemical catalog #383058) and 9.3 grams of hydrogen peroxide (35%, Aldrich Chemical catalog #349887) in 187.5 mL of deionized water. The mixture was stirred for a few minutes until all of the liquid was absorbed. The wet gel was spread onto a plastic dish and set in front of an electric fan to dry at room temperature for three days. The dried material was collected and lightly ground in a mortar and pestle to a consistency resembling that of the starting SAP powder.

Example 2: Treatment of a SAP with Zinc Acetate and Hydrogen Peroxide (Sample ZNP-2B)

A procedure substantially similar to that described in Example 1 was used, except that the zinc acetate and hydrogen peroxide concentrations were lower. The treatment solution was prepared using 1.5 grams of zinc acetate, 3.5 grams of HP and 195 mL of water.

Example 3: Treatment of a SAP with Zinc Acetate (Sample ZNP-2C)

The procedure of Example 2 was followed, except that the hydrogen peroxide was omitted.

Example 4: Treatment of a SAP with Hydrogen Peroxide (Sample ZNP-2D)

The procedure of Example 2 was followed, except that the zinc acetate was omitted.

Example 5: Treatment of a SAP with Hydrogen Peroxide (Sample HP1-A)

The procedure of Example 4 was followed, except that 6 grams of hydrogen peroxide and 94 grams of deionized water were used.

Example 6: Treatment of a SAP with Hydrogen Peroxide (Sample HP1-B)

The procedure of Example 4 was followed, except that 6 grams of hydrogen peroxide and 94 grams of deionized water were used, and the sample was dried in an oven set at 80° C. for 3 hours. Absorbance and antimicrobial efficacy results (see below) for the heat treated powders were not different from the results for the powders dried at room temperature. This indicates good thermal stability for the compositions.

Example 7: Heat Treatment of an Antimicrobial SAP Powder

Samples of the materials prepared in Examples 2 and 4 were placed in uncovered beakers in an oven set at 60° C. for 72 hours to test the thermal stability of the antimicrobial SAP powders. Absorbance and antimicrobial efficacy results (see below) for the heat treated powders were not different from the results for the as-produced powders. This indicates good thermal stability for the compositions.

Example 8: Treatment of Carboxymethylcellulose (CMC) with Hydrogen Peroxide (Sample 121208C)

Ten grams of a carboxymethylcellulose (CMC) powder were treated with 50 mL of solution prepared by mixing 5 grams of 35% HP with 45 mL of distilled water. The mixture was stirred and kneaded for several minutes until a uniform consistency was obtained. The resulting antimicrobial CMC composition was then air-dried for 72 hours and lightly ground with a mortar and pestle.

Example 9: Fluid Absorbance of the Antimicrobial SAP Materials Prepared in the Above Examples Each powder from Examples 1 to 8 was placed into a plastic centrifuge tube with phosphate buffered saline (PBS, pH=7.4) at a ratio of 0.2 grams of powder to 10 mL of PBS. The tubes were shaken and left to sit for one hour. The tubes were shaken again and then centrifuged at approximately 2000 rpm for ten minutes. The ratio of swollen SAP gel to supernatant liquid in each tube was used to calculate the absorption capacity of the antimicrobial SAP powders.

Untreated SAP powder absorbed approximately 45 times its weight of PBS. The materials of the above Examples all absorbed at least 35 times their weight of PBS, with the exception of the material of Example 1, which only absorbed 30 times its weight.

Example 10: Observation of Non-Leaching Antimicrobial Effects

PBS solution removed from each tube prepared for the absorbance studies described in Example 9 was placed onto agar plates with freshly inoculated lawn-spreads of *S. aureus* bacteria, and it was found after overnight incubation that there was no inhibition of bacterial growth in the areas where the solutions were placed. This indicates that there is no significant leaching of antimicrobial components (such as HP or zinc) into the solutions. Accordingly, the antimicrobial effects described below are from contact of the bacteria with the solid gel formed by absorption of PBS into the SAP powders. In other words, the mechanism does not appear to be a result of HP simply being trapped inside the dried SAP matrix, or release of sequestered HP from the antimicrobial composition.

Example 11: Evaluation of Antimicrobial Performance of SAP Materials

Each sample was evaluated in triplicate. Experimental powders (0.25 g) were weighed into 50-ml conical polypropylene centrifuge tubes and 11.5 mL of PBS (phosphate buffered saline, 1×, Fisher Scientific #BP-399-1) was added to each tube by pipette. Untreated SAP control test samples were prepared similarly in triplicate. A $10^{-1}$ inoculum of *Escherichia coli* (ATCC #15597) or *Staphylococcus aureus* (ATCC #6538) was prepared from a $10^{-2}$ dilution of an overnight culture in TSB (tryptic soy broth, Becton Dickinson Bacto™, REF 211825) of a glycerol stock. To each tube containing the powders to be tested, 1 mL of inoculum was added. Tubes were vortexed for 10 seconds and then placed on a vertical rotating wheel and rotated at 25 rpm for 24 hours at room temperature. Tubes were then removed from the wheel and 10 mL of Letheen broth was added to each tube by pipette. Tubes were vortexed at the maximum speed for 30 seconds. Dilutions were then made and plated on appropriate agar using the standard pour plate method. Plates were incubated at 37° C. overnight, and then the bacterial colonies were enumerated. The results are summarized below, and expressed as "log reduction" of viable organisms, in comparison to the growth observed in the tubes containing untreated SAP powder.

| Sample# | Description | Avg. Log Reduction | Organism |
| --- | --- | --- | --- |
| ZNP-1 | ZA + HP | 6.21* | EC |
| ZNP-1 | ZA + HP | 5.96* | SA |
| ZNP-2B | ZA + HP | 6.21* | EC |
| ZNP-2C | ZA | 1.75 | EC |
| ZNP-2D | HP | 5.61 | EC |
| HP1-A | HP | 6.49* | EC |
| HP1-B | HP | 6.49* | EC |
| 121208C | HP on CMC | 6.49* | EC |

SA = *S. Aureus*
EC = *E. Coli*
HP = Hydrogen Peroxide
ZA = Zinc Acetate
*= Full Kill The above results indicate that HP is the primary agent responsible for the antimicrobial activity, and that the antimicrobial contribution by the zinc component is minimal.

Example 12: Evaluation of Antimicrobial Performance of SAP Materials after Prolonged Storage The materials and procedures of Example 11 were used. Antimicrobial SAP materials were stored in sealed containers at room temperature for eight (8) months, and then tested for antimicrobial activity. The following results were obtained, which indicate that the materials are stable during storage:

| Sample# | Description | Avg. Log Reduction | Organism |
| --- | --- | --- | --- |
| ZNP-1 | ZA + HP | 7.08* | EC |
| ZNP-2B | ZA + HP | 7.08* | EC |
| ZNP-2C | ZA | 2.08 | EC |
| ZNP-2D | HP | 7.08* | EC |

EC = *E. Coli*
HP = Hydrogen Peroxide
ZA = Zinc Acetate
*= Full Kill

Example 13: Iodometric Titration of Antimicrobial SAP Powders to Demonstrate and Quantify Sequestration of HP, and Non-Leaching Properties Antimicrobial SAP powders described in the above examples were titrated to determine the amount of HP contained therein which is available for antimicrobial action. All SAP powders had been stored for greater than one year prior to titration.

Principle:

Hydrogen peroxide in the sample reacts with excess iodide in the presence of an ammonium molybdate catalyst to stoichiometrically produce triiodide ions. The triiodide ion concentration is then determined titrimetrically with a standard thiosulfate solution. The following method was adapted from methods published by Solvay Chemicals. Inc. [TDS HH-125 "Determination of Hydrogen Peroxide ($H_2O_2$) Residual in Fiber Matrices", and TDS XX-122, "Determination of Hydrogen Peroxide Concentration (0.1% to 5%)"].

Preparation of Reagents:

All reagents used were analytical reagent grade and only deionized water was used.

1. Potassium iodide (10%): In a 2-L beaker, 100 g of potassium iodide (KI) was dissolved in 1000 mL of water, and stored in a dark glass or opaque, capped bottle.
2. Acid Mixture: In a 2-L beaker, was dissolved 0.18 g of ammonium molybdate $((NH_4)_6Mo_7O_{24}.4H_2O)$ in 750 mL of water. While stirring, 300 mL of concentrated sulfuric acid ($H_2SO_4$) was slowly added, and stored in a glass container.
3. Sodium Thiosulfate Solution (0.100N): 49.63 g of sodium thiosulfate ($Na_2S_2O_3.5H_2O$) was transferred to a 2-L volumetric flask, and 400 mL of water was added and agitated until dissolution was complete, and diluted to volume, mixed well, and stored in an amber or opaque, capped bottle.

The normality of this solution remained between 0.099N and 0.101N for at least one month. Alternatively, standard sodium thiosulfate solution was purchased from a laboratory supply company.

Starch Solution (10 g/L): One gram of soluble starch was weighed into a 150-mL beaker. While stirring, about 5 mL of water was gradually added until a paste formed. The paste was then added to 100 mL of boiling water. The mixture was cooled, 5 g of potassium iodide (KI) was added, and stirred until dissolution was complete, and then transferred to a plastic bottle. The Following Analysis Procedure was then followed:
1. Weigh 1 g of antimicrobial SAP powder ("sample") into a 125-mL Erlenmeyer flask. Record sample weight to the nearest 0.01 g.
2. Add 50 mL of distilled water and swirl for 15 seconds to mix.
3. Place flask in a water bath and heat at 50 C, while agitating, for 2 hours. Let cool for 15 minutes.
4. Add 20 mL of 10% potassium iodide solution to the flask. Swirl to mix.
5. Add 25 mL of $H_2SO_4$/ammonium molybdate solution to the flask. Swirl to mix.
6. Let stand for 5 minutes.
7. Using a magnetic stirrer, begin stirring the slurry.
8. Using a 50-mL class-A burette, titrate the flask contents with the standard 0.100N sodium thiosulfate solution until the color turns to a bright yellow hue.
9. Add a few drops of starch indicator to the flask.
10. Resume titrating until the dark blue color of the solution turns clear.
11. Record the total volume of sodium thiosulfate dispensed as '$A_o$'.
12. Repeat Steps 4 through 10 with pure water and record the volume of sodium thiosulfate dispensed as 'B'.
13. Let the slurry stand for a predetermined length of time to measure the amount of additional sequestered HP that is released (i.e. 24 hours, 48 hours, etc.). Resume stirring and titrate as in Step 10, above. Record the total volume of sodium thiosulfate as '$A_T$'.

The results were calculated according to the following:

$$\text{Hydrogen peroxide, \% w/w} = \frac{(\sum A_i - B) * (N) * (1.7007)}{C}$$

Where:
$\Sigma A_i$=sum of the titration volumes for sample (mL)
B=titration volume for blank (mL)
C=powder sample weight
N=normality of the sodium thiosulfate solution Results:
The following results were obtained:

| Sample Name | Initial [HP] (%) | [HP] @ 24 hours[1] | [HP] @ (X) hours[2] |
|---|---|---|---|
| ZnP-1 | 0.61 | 0.98 | 2.16 (144 h) |
| ZnP-2B | 0.51 | 0.51 | — |
| ZnP-2C (no HP) | 0.09 | 0.09 | — |
| ZnP-2D (no Zn) | 0.36 | 0.56 | 1.05 (120 h) |

[1]Cumulative % HP at 24 h
[2]Cumulative % HP at indicated hours

The results clearly demonstrate that a significant amount of sequestered active HP is released from the samples, even after storage for over one year in the dry state. Furthermore, these results demonstrate that active HP is released in a sustained manner over a period of time (i.e. controlled-release of HP, which has oxidative or antimicrobial capacity) in the presence of an oxidative demand (in this case the presences of iodide ion).

In light of the general disclosure provided herein above, with respect to the manner of practicing this inventive method, those skilled in the art will appreciate that this disclosure enables the practice of the inventive method according to the aspects and embodiments disclosed above. However, the following experimental details are provided to ensure a complete written description of this invention, including the best mode thereof. However, it will be appreciated that the scope of this invention should not be construed in terms of the specific examples provided. Rather, the scope of this invention is to be apprehended with reference to the claims appended hereto, in light of the complete description of this inventive method constituted by this entire disclosure.

It is to be understood that the present invention may have various other embodiments. Furthermore, while the form of the invention herein shown and described constitutes a preferred embodiment of the invention, it is not intended to illustrate all possible forms thereof. It will also be understood that the words used are words of description rather than limitation, and that various changes may be made without departing from the spirit and scope of the invention disclosed. The scope of the invention should not be limited solely to the examples given.

The invention claimed is:
1. A method of making an antimicrobial superabsorbent polymer in the form of a dried powder or granular material comprising the steps:
   (a) swelling to uniformly wet a cross-linked fully- or partially-neutralized salt of an acrylic acid-based superabsorbent polymer with an aqueous treatment solution comprising 0.005 grams to 0.2 grams of hydrogen peroxide per gram of the acrylic acid-based superabsorbent polymer, and followed by
   (b) thoroughly drying the swelled acrylic acid-based superabsorbent polymer to form the antimicrobial superabsorbent polymer,
   wherein an antimicrobial superabsorbent polymer consisting of an acrylic acid-based superabsorbent polymer and hydrogen peroxide is produced, whereby peroxide is sequestered or bound in a non-volatile manner within or on the surface of the dried antimicrobial superabsorbent polymer, wherein said antimicrobial superabsorbent polymer provides sustained release of hydrogen peroxide.
2. The method of claim 1, wherein said aqueous treatment solution comprises 0.02 grams to 0.15 grams of hydrogen peroxide per gram of acrylic acid-based superabsorbent polymer.
3. The method of claim 1, wherein said cross-linked fully- or partially-neutralized salt of an acrylic acid-based polymer is a cross-linked hydrophilic sodium salt form of a partially neutralized acrylic acid polymer.
4. The method of claim 1, further comprising an assay step wherein a ratio of polymer to liquid of about 0.2 grams of the antimicrobial superabsorbent polymer to approximately 1,000,000 viable bacteria in about 11 milliliters of an aqueous liquid produces at least a 3-log reduction of viable bacteria in said aqueous liquid.

* * * * *